United States Patent [19]
Ryder et al.

[11] Patent Number: 4,701,467
[45] Date of Patent: Oct. 20, 1987

[54] TOLRESTAT AS ANTI-HYPERTENSIVE AGENT

[75] Inventors: Steven W. Ryder, St. James; David G. Shand, New York; John F. Mullane, Pelham, all of N.Y.

[73] Assignee: American Home Products Corporation, New York, N.Y.

[21] Appl. No.: 853,068

[22] Filed: Apr. 17, 1986

[51] Int. Cl.$^4$ .......................................... A61K 31/275
[52] U.S. Cl. .................................................. 514/524
[58] Field of Search ........................................ 514/524

[56] References Cited
U.S. PATENT DOCUMENTS
4,568,693  2/1986  Sestanj et al. ..................... 514/524

Primary Examiner—Frederick E. Waddell
Attorney, Agent, or Firm—John W. Routh

[57] ABSTRACT

A method is disclosed for lowering blood pressure by administering an effective amount of tolrestat.

5 Claims, No Drawings

TOLRESTAT AS ANTI-HYPERTENSIVE AGENT

BACKGROUND OF THE INVENTION (a) Field of the Invention

This invention relates to a novel therapeutic use of N-[[5-(trifluroomthyl)-6-methoxy-1-naphthenyl]-thioxomethyl]-N-methylglycine. More specifically this invention relates to a method for lowering blood pressure in humans.

(b) Prior Art

The active agent of this invention, N-[[5-(trifluoromethyl)-6-methoxy-1-napthenyl]-thioxomethyl]-N-methylglycine or a therapeutically acceptable salt thereof, is disclosed in U.S. Pat. No. 4,568,693, issued Feb. 4, 1986. This active agent, hereinafter designated by its generic name tolrestat, previously has been reported to be useful in preventing or relieving diabetic complications such as cataracts, neuropathy, nephropathy and retinopathy (See U.S. Pat. No. 4,568,693). We have now found unexpectedly that tolrestat, either in its free acid form or in its therapeutically acceptable salt form, is useful for lowering blood pressure in humans, and particularly humans suffering from diabetes mellitus.

This finding, coupled with the fact that tolrestat is a relatively safe drug, renders the method of this invention particularly useful and advantageous.

SUMMARY OF THE INVENTION

According to this invention a method is provided for lowering blood pressure in a human in need of such treatment, which comprises administering to the human an effective amount of tolrestat, or a therapeutically acceptable salt thereof.

DETAILS OF THE INVENTION

According to the present method, tolrestat, either in its free acid form or in the therapeutically acceptable salt form, is employed as the active agent. Examples of suitable salt forms are described in U.S. Pat. No. 4,568,693 and include the sodium, potassium, magnesium triethylamine and benzylamine salt forms. A preferred salt form is the sodium salt, i.e. tolrestat sodium.

Tolrestat or a therapeutically acceptable addition salt thereof is administered to humans suffering from high blood pressure either orally or parenterally. For many reasons oral administration is preferred.

While tolrestat or a therapeutically acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 4,568,693, herein incorporated by reference in its entirety.

When utilizing tolrestat or one of its above-noted salts as agents for lowering blood pressure, the total dose of active agent can range from 0.1 to 20 mg per kilogram of body weight per day with a preferred dosage range of from 50 to 400 milligrams per day. Generally, a parenteral dose or an oral dose is administered in one to four applications per day. Such doses are considered to be an effective amount when, following their administration, a decrease in blood pressure is experienced by the patient.

The effectiveness of tolrestat or its therapeutically acceptable salts as agents for lowering blood pressure in a human has been demonstrated in human clinical trials.

In a 52-week double-blind clinical trial with 550 diabetic patients (diabetes mellitus), minor but statistically significant changes from baseline occasionally occured in the systolic diastolic blood pressure measurements. obtained in the tolrestat treatment groups, 443 patients, (50 to 200 milligrams per day) but not the placebo treatment group, 107 patients, at select visits. These results are presented in Table I.

TABLE I
Significant Differences Between Tolrestat and Placebo Treatment Groups in Changes from Baseline of Blood Pressure (mm Hg)

| Parameter | Week of Visit | Placebo Change from Baseline (Least Squares Mean + SE) | Tolrestat Treatment Group: Change from Baseline (Least Squares Mean + SE) |
| --- | --- | --- | --- |
| Systolic Blood Pressure | 4 | +0.6 ± 1.7 | 100 mg QD: −4.4 ± 1.7 |
|  | 8 | +2.8 ± 1.8 | 100 mg QD: −4.5 ± 2.0 |
|  |  |  | 200 mg QD: −4.9 ± 1.7 |
|  | 12 | +2.1 ± 1.9 | 100 mg QD: −4.4 ± 2.0 |
|  |  |  | 200 mg QD: −4.5 ± 1.8 |
|  | 24 | +1.4 ± 1.9 | 100 mg QD: −4.8 ± 2.1 |
|  |  |  | 200 mg QD: −4.3 ± 1.9 |
|  | 32 | +0.4 ± 2.0 | 100 mg QD: −5.8 ± 2.2 |
|  | 42 | +1.6 ± 2.0 | 50 mg QD: −5.3 ± 2.2 |
|  |  |  | 200 mg QD: −4.3 ± 2.0 |
| Diastolic Blood Pressure | 2 | +0.9 ± 1.0 | 100 mg QD: −3.3 ± 1.0 |
|  | 12 | +1.2 ± 1.1 | 100 mg QD: −2.0 ± 1.1 |
|  |  |  | 200 mg QD: −1.9 ± 1.0 |
|  |  |  | 100 mg BID: −2.2 ± 1.1 |
|  | 24 | +0.6 ± 1.1 | 50 mg QD: −2.6 ± 1.2 |
|  |  |  | 100 mg QD: −3.0 ± 1.2 |
|  |  |  | 200 mg QD: −2.4 ± 1.1 |
|  |  |  | 100 mg BID: −3.2 ± 1.3 |
|  | 32 | +1.1 ± 1.0 | 50 mg QD: −2.7 ± 1.1 |
|  |  |  | 100 mg QD: −3.2 ± 1.1 |

In another double-blind clinical trial with diabetic patients lasting 8 weeks, 86 patients received 400 milligrams q.d. of tolrestat, 85 patients received 200 milligrams b.i.d. of tolrestat and 89 patients received placebo.

In the 8-week study, a statistically significant decrease from baseline systolic blood pressure occurred at the Week 4 visit for both the tolrestat 200 mg b.i.d.(−4.4±1.8 nn Hg) and the tolrestat 400 mg q.d.(−3.8±1.9 mm Hg) group, while the systolic blood pressure of the placebo group did not change.

In this same trial, a statistically significant decrease from baseline diastolic blood pressure occurred at the Week 4 visit (−2.6±1.0 mm Hg) in the tolrestat 400 mg q.d. group. This decrease was statistically significantly lower than the change from baseline noted in the placebo group.

The method of this invention is particularly beneficial for lowering blood pressure in a diabetic patient suffering from diabetes mellitus although the decrease in blood pressure is independent of neuropathy.

I claim:

1. A method for lowering blood pressure in a diabetic human in need of such treatment which comprises administering to the diabetic human an effective amount of tolrestat or a therapeutically acceptable salt thereof.

2. The method of claim 1 in which the effective amount of tolrestat is within the range of from 0.1 to 20 mg per kilogram of body weight.

3. The method of claim 1 in which the effective amount of tolrestat is within the range of from 50 to 400 milligrams per day.

4. The method of claim 1 in which the therapeutically acceptable salt is the sodium salt.

5. The method of claim 1 in which the human being treated suffers from diabetes mellitus.

* * * * *